(12) United States Patent
Magness

(10) Patent No.: US 12,419,775 B2
(45) Date of Patent: Sep. 23, 2025

(54) NASAL DEVICE FOR IMPROVING NASAL BREATHING

(71) Applicant: R. Joseph Magness, Orem, UT (US)

(72) Inventor: R. Joseph Magness, Orem, UT (US)

( * ) Notice: Subject to any disclaimer, the term of this patent is extended or adjusted under 35 U.S.C. 154(b) by 1193 days.

(21) Appl. No.: 17/027,668

(22) Filed: Sep. 21, 2020

(65) Prior Publication Data

US 2021/0085509 A1 Mar. 25, 2021

Related U.S. Application Data

(60) Provisional application No. 62/959,720, filed on Jan. 10, 2020, provisional application No. 62/903,170, filed on Sep. 20, 2019.

(51) Int. Cl.
*A61F 5/08* (2006.01)
*B29C 64/393* (2017.01)
(Continued)

(52) U.S. Cl.
CPC .............. *A61F 5/08* (2013.01); *B29C 64/393* (2017.08); *B33Y 50/02* (2014.12); *B33Y 80/00* (2014.12); *B29L 2031/753* (2013.01)

(58) Field of Classification Search
CPC . A61F 5/08; A61F 5/56; B29C 64/393; B29C 64/386; B33Y 50/00; B33Y 50/02;
(Continued)

(56) References Cited

U.S. PATENT DOCUMENTS

| 1,034,123 A | 7/1912 | Knowlson |
| 1,077,574 A | 11/1913 | Woodward |

(Continued)

FOREIGN PATENT DOCUMENTS

| RU | 2514120 C1 | 4/2014 |
| RU | 2618187 C1 | 5/2017 |
| WO | 2012/058660 A1 | 5/2012 |

OTHER PUBLICATIONS

Translation of RU 2514120.
(Continued)

*Primary Examiner* — Diane D Yabut
(74) *Attorney, Agent, or Firm* — Young Basile Hanlon & MacFarlane, P.C.

(57) ABSTRACT

A method of manufacturing a device for facilitating or improving nasal breathing in a human user is disclosed. The method may begin with receiving a digital scan of an exterior of a nose of a human user. Based on the digital scan, a first virtual three-dimensional model of the exterior of the nose may be created. Once created, the first virtual three-dimensional model may be deformed to produce a second virtual three-dimensional model of the exterior of the nose. The deforming may include moving selected surfaces outward to simulate the flexible tissues on the sides of the nose being in an improved or optimum position for nasal breathing. Based on the second virtual three-dimensional model, a virtual three-dimensional model of a nasal dilation device may be created. An additive manufacturing process may be used to produce a tangible instance of the nasal dilation device, which may be delivered to the human user. When worn by the human user, the nasal dilation device may hold the flexible tissues on the sides of the user's nose in an improved or optimum position for nasal breathing.

15 Claims, 19 Drawing Sheets

(51) Int. Cl.
  *B33Y 50/02* (2015.01)
  *B33Y 80/00* (2015.01)
  *B29L 31/00* (2006.01)

(58) Field of Classification Search
  CPC ............... B33Y 80/00; B29L 2031/753; A61B 2034/104; A61B 2034/105; A61B 2034/108
  See application file for complete search history.

(56) References Cited

U.S. PATENT DOCUMENTS

| | | | |
|---|---|---|---|
| 5,476,091 A | 12/1995 | Johnson | |
| 5,922,006 A | 7/1999 | Sugerman | |
| 6,015,425 A | 1/2000 | Altadonna, Jr. | |
| 7,318,438 B2 | 1/2008 | Brown | |
| 7,461,651 B2 | 12/2008 | Brown | |
| 8,047,201 B2 | 11/2011 | Guyuron et al. | |
| 8,182,504 B2 | 5/2012 | Yazdi | |
| 8,616,198 B2 | 12/2013 | Guyuron et al. | |
| 8,834,512 B1 | 9/2014 | Brown et al. | |
| 9,381,332 B2 | 7/2016 | Judd | |
| 10,188,812 B2 | 1/2019 | Toriumi | |
| 2010/0042139 A1* | 2/2010 | Honegger | A61F 5/08 606/204.45 |
| 2010/0228282 A1* | 9/2010 | Fenton | A61F 5/08 606/204.45 |
| 2016/0338869 A1* | 11/2016 | Kurzban | A61F 5/08 |

OTHER PUBLICATIONS

Translation of RU 2618187.
Written Opinion of the International Searching Authority for International Application No. PCT/US2020/051888, mailing date Jan. 21, 2021.

* cited by examiner

NASAL DEVICE FOR IMPROVING NASAL BREATHING

RELATED APPLICATIONS

This application claims the benefit of U.S. Provisional Patent Application Ser. No. 62/903,170 filed Sep. 20, 2019 and U.S. Provisional Patent Application Ser. No. 62/959,720 filed Jan. 10, 2020, both of which are hereby incorporated by reference.

BACKGROUND

1. Field of the Invention

This invention relates to nasal devices and, more particularly, to novel systems and methods for improving nasal breathing of a human user.

2. Background Art

An external nasal dilator is typically secured to the skin of the nose of a human user via an adhesive. Once applied to the nose, an external nasal dilator may lift the outer wall tissues of the nostrils. This may dilate the nasal passage and reduce resistance to airflow during nasal breathing. One disadvantage of such an external nasal dilator is that the skin of the user must be substantially oil free for sufficient adhesion to occur. Accordingly, what is needed is a device that improves nasal breathing without requiring adhesive.

BRIEF DESCRIPTION OF THE DRAWINGS

The features of the present invention will become apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF SELECTED EMBODIMENTS

Figure 1:
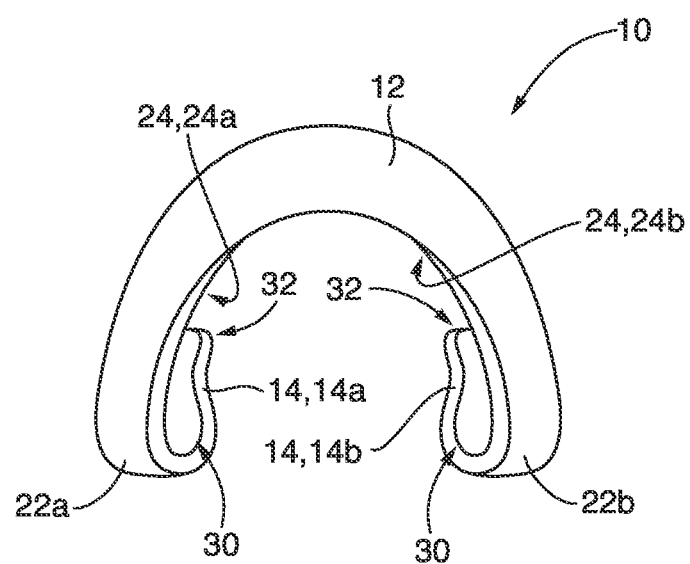
FIG. 1 is a front view of one embodiment of a nasal device in accordance with the present invention.
Figure 2:
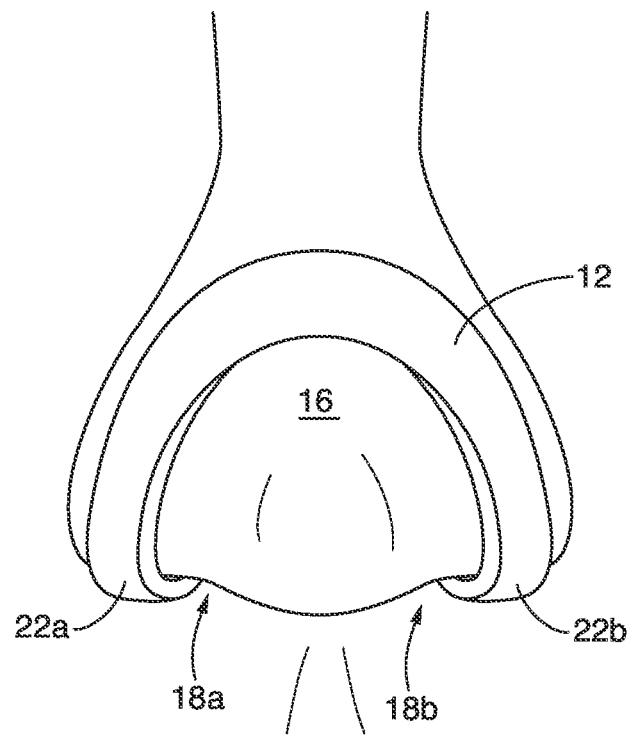
FIG. 2 is a front view of the nasal device of FIG. 1 applied to a human user.
Figure 3:
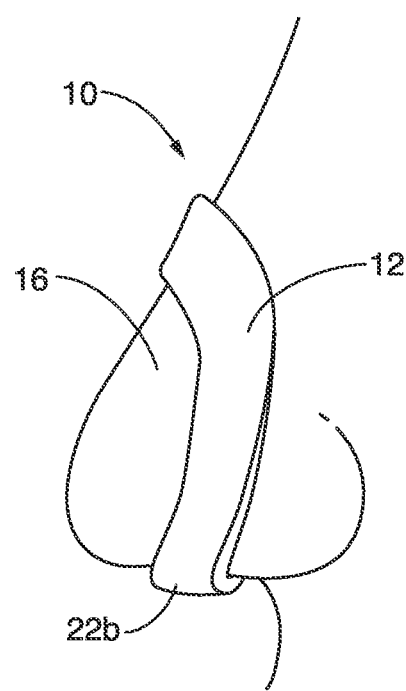
FIG. 3 is a side view of the nasal device of FIG. 1 applied to a human user.
Figure 4:
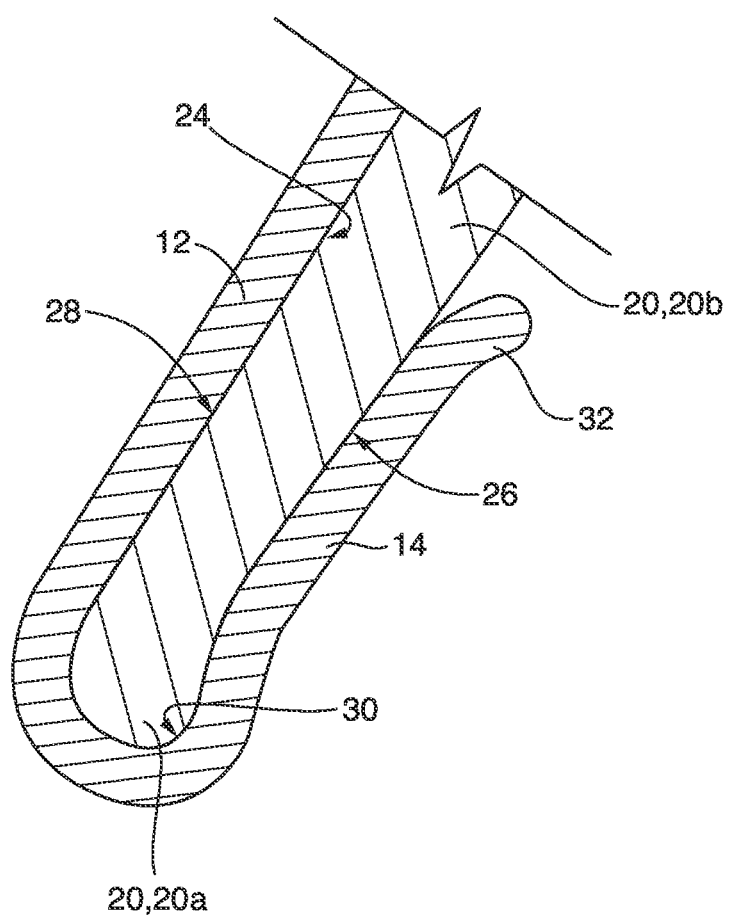
FIG. 4 is a cross-sectional view of a portion of the nasal device of FIG. 1 applied to a human user.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Referring to FIGS. 1-4, a nasal device 10 in accordance with the present invention may include a standard 12 and one or more regulators 14 (e.g., two regulators 14). A standard 12 may be sized and shaped to extend over a portion of an exterior of a nose 16 of a human user. In certain embodiments, a standard 12 may be sized and shaped to extend from one nasal opening 18a upward over the flexible tissues 20 (e.g., the greater alar cartilage, lateral cartilage, surrounding skin, etc.) of one side of the nose, over the cartilage of septum, downward over the flexible tissues 20 of the other side of the nose, and to the other nasal opening 18b.

A standard 12 may have two ends 22a, 22b. When applied to the nose 16 of a user, a first end 22a of a standard 12 may be positioned proximate a first nasal opening 18a and a second end 22b of the standard 12 may be positioned proximate a second nasal opening 18b.

In selected embodiments, a first regulator 14a may connect to and extend from a first end 22a of a standard 12. A second regulator 14b may connect to and extend from a second end 22b of a standard 12. When applied to the nose 16 of a user, a first regulator 14a may extend into a first nasal opening 18a and a second regulator 14b may extend into a second nasal opening 18b.

An underside 24 of a standard 12 may define an improved or optimal location of the flexible tissues 20 that form the outer wall of a corresponding nostril. For example, an underside 24a corresponding to one half of a standard 12 may define an improved or optimal location of the flexible tissues 20 that form the outer wall of a first nostril. Accordingly, when the flexible tissues 20 that form the outer wall of the first nostril abut that underside 24a, the first nostril may be positioned for improved or optimized nasal breathing. Similarly, an underside 24b corresponding to the other half of the standard 12 may define an improved or optimal location of the flexible tissues 20 that form the outer wall of a second nostril. Accordingly, when the flexible tissues 20 that form the outer wall of the second nostril abut that underside 24b, the second nostril may be positioned for improved or optimized nasal breathing.

Regulators 14 may be sized, shaped, and positioned to hold certain flexible tissues 20 of a nose 16 to a corresponding standard 12. That is, a regulator 14 may push against an inner surface 26 of the flexible tissues 20 until an outer surface 28 of the flexible tissues 20 abuts an underside 24 of a standard 12. Accordingly, when the flexible tissues 20 that form the outer wall of a first nostril are pushed by a first regulator 14a against an underside 24a corresponding to one half of a standard 12, then the first nostril may be positioned for improved or optimized nasal breathing. Similarly, when the flexible tissues 20 that form the outer wall of a second nostril are pushed by a second regulator 14b against an underside 24b corresponding to the other half of a standard 12, then the second nostril may be positioned for improved or optimized nasal breathing.

In selected embodiments, the flexible tissue 20a forming or defining a nasal opening 18 may be somewhat bulbous or thicker than the flexible tissue 20b further up the nose 16. In such embodiments, one or more corresponding regulators 14 may define a slightly larger cavity 30 to accommodate this bulbous or thicker flexible tissue 20b. In certain embodiments, the interaction between the bulbous or thicker flexible tissue 20b and a corresponding larger cavity 30 may create a detent of sorts that may tend to hold a nasal device 10 in a fully installed or seated configuration. In certain embodiments, the tip 32 of a regulator 14 may be curved, smoothed, ramped, or a combination or sub-combination thereof to make application of the nasal device 10 to a user a painless and easy process.

A nasal device 10 in accordance with the present invention may be formed of a material having sufficient thickness and rigidity to flex the flexible tissues 20 rather than be flexed by those tissues 20. Accordingly, in use, the flexible tissues 20 may conform to the standard 12 while the standard 12 remains substantially unchanged. In selected embodiments, a nasal device 10 may comprise a standard 12 and two regulators 14a, 14b monolithically formed as a single piece of polymeric material.

Figure 5:
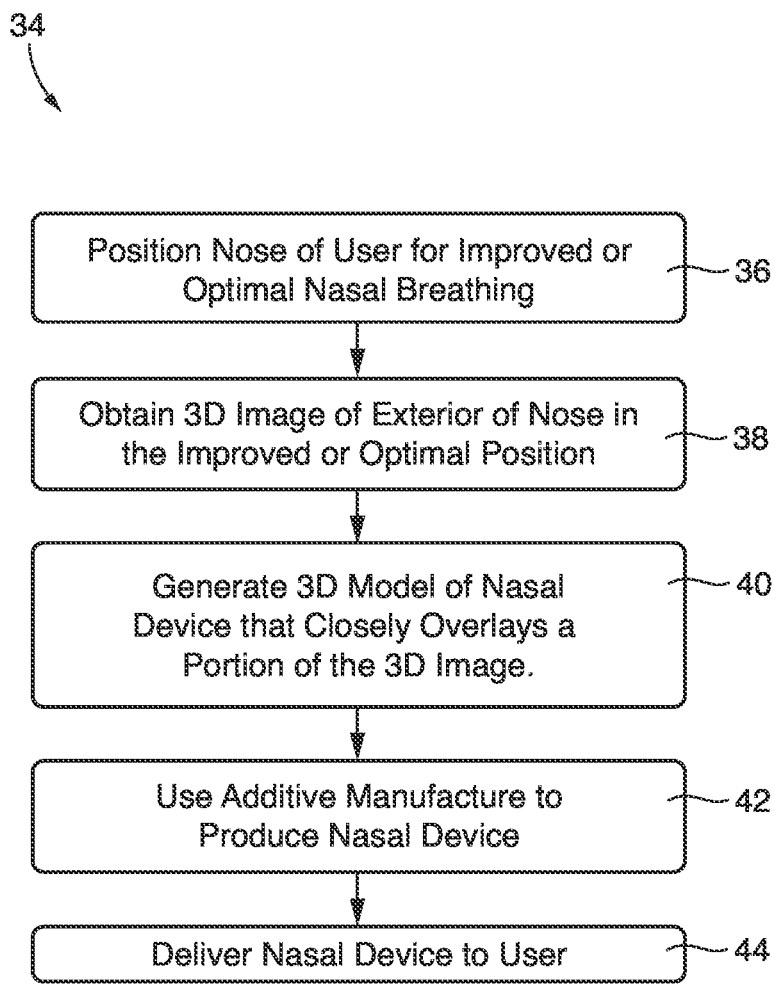
FIG. 5 is a block diagram of one embodiment of a method in accordance with the present invention.

Referring to FIG. 5, a nasal device 10 in accordance with the present invention may be manufactured in any suitable manner. In selected embodiments, a standard 12 and two regulators 14a, 14b may be made as a monolithic unit using three-dimensional printing. This may enable a nasal device 10 to be custom made for each user. Custom manufacture of a nasal device 10 in accordance with the present invention may ensure that the nasal device 10 is both comfortable to wear and effective (e.g., maximally effective) for each user.

For example, in one method 34, a nose 16 of a user may be positioned 36 for improved or optimal breathing. This may involve examining certain internal features of a user's nostrils and deflecting certain flexible tissues 20 of the user's nose 16 so as to improve or optimize the flow of air through one or both nostrils. In selected embodiments, once the improved or optimized position is identified, steps may be taken to hold the flexible tissues 20 of the nose 16 in the improved or optimized position(s). This may be accomplished by inserting filler or packing material into one or both nostrils.

Once the nose 16 of the user is properly positioned, a three-dimensional model of the exterior of a user's nose may be obtained 38 or generated via a digital scan. The three-dimensional model of the nose may be used to create 40 a three-dimensional model of a nasal device 10. Specifically, a standard 12 may be shaped to match the improved or optimized position of the nose 16 of a user. Accordingly, a standard 12 may track (e.g., closely follows selected contours of) the nose 16 so positioned. Moreover, one or more regulators 14 may be digitally defined so as to appropriately fit and extend into corresponding nasal openings 18.

The gap between a standard 12 and a regulator 14, the size and shape of a cavity 30 defined by a regulator 14, the length of a regulator 14, and the like may be customized. That is, they may be based on measurements collected from the corresponding user. Alternatively, one or more such features may be determined based on certain average or expected measurements. Accordingly, in certain embodiments, a computer-aided drafting (CAD) application or the like may be used to import one or more regulators 14 into the three dimensional model. The regulators 14 may be a predefined, standard part. Accordingly, they may be imported and located as desired.

Once a standard 12 and one or more regulators 14 are properly positioned within a digital three dimensional model, the interfaces between the various components may be filled and/or smoothed so as to provide the desired comfort and functionality. The completed digital three dimensional model may then be printed 42 in a polymeric material using a three-dimensional printing process. The resulting nasal device 10 may then be delivered 44 to the corresponding user.

Figure 6:
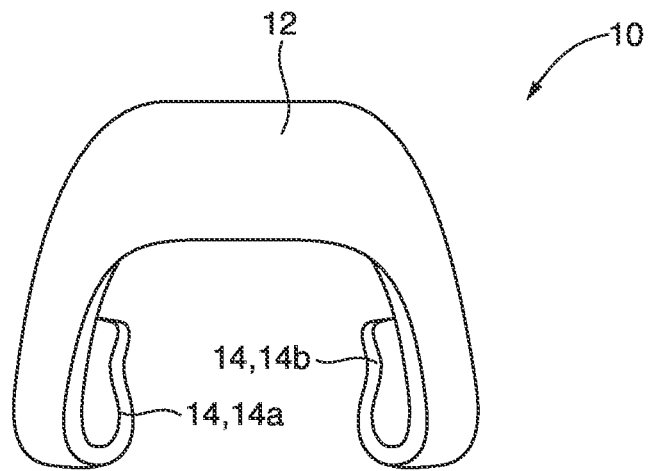
FIG. 6 is a front view of an alternative embodiment of a nasal device in accordance with the present invention.
Figure 7:
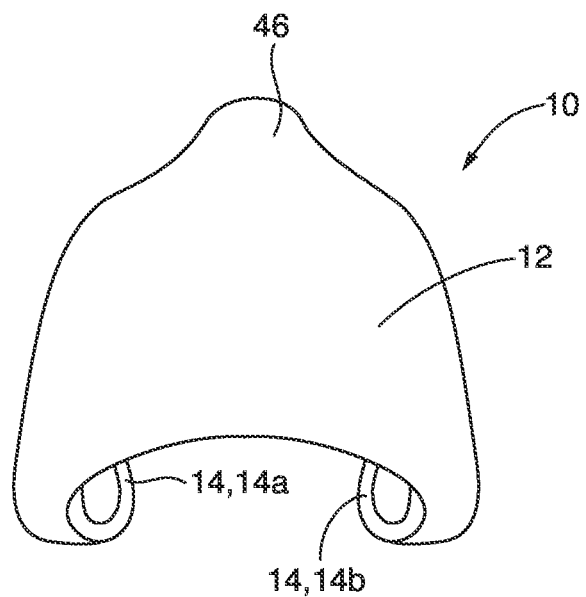
FIG. 7 is a front view of another alternative embodiment of a nasal device in accordance with the present invention.
Figure 8:
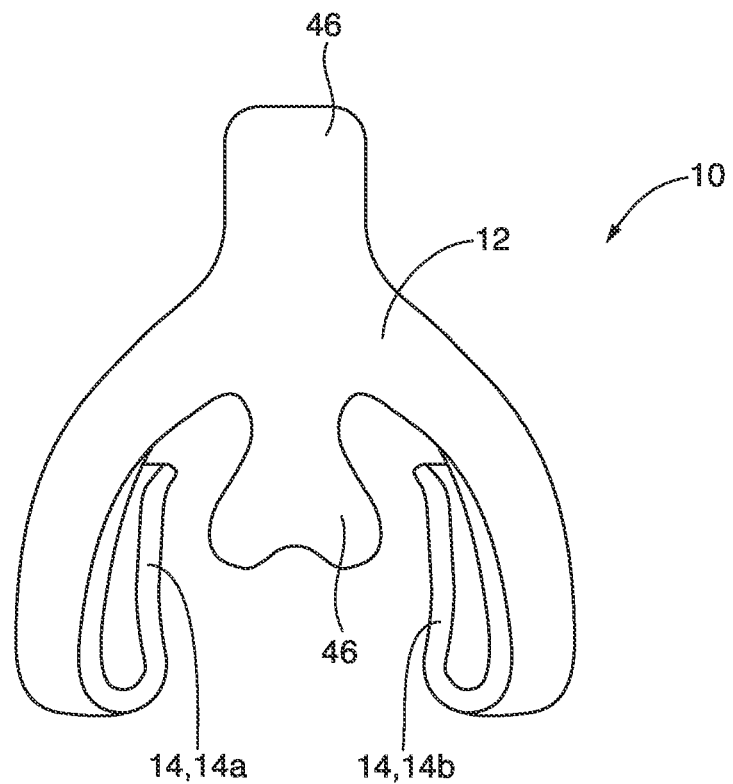
FIG. 8 is a front view of another alternative embodiment of a nasal device in accordance with the present invention.

Referring to FIGS. 6-8, a standard 12 in accordance with the present invention may have any suitable shape. Accordingly, a standard 12 may cover or closely track more or less of the exterior of a nose 16 in an improved or optimized position. Greater coverage of the nose 16 may enable or support more shaping of or control over the flexible tissues 20. Lesser coverage of the nose 16 may make the device 10 lighter and enable the skin to interact more normally with the surrounding air (e.g., "breathe" better).

In selected embodiments, a standard 12 may include one or more extensions 46. The one or more extensions 46 may be sized and positioned so as to align with and extend along a ridge of a nose 16. Accordingly, one or more extensions 46 may tend to stabilize a standard 12 with respect to a nose 16.

Regulators 14 in accordance with the present invention may have any suitable length. Accordingly, regulators 14 may extend any suitable distance into the nostrils of a user. In general, a regulator 14 may extend sufficiently to hold corresponding flexible tissue 20 to a standard 12 and insufficiently to become a nuisance to or uncomfortable for the user.

Figure 9:
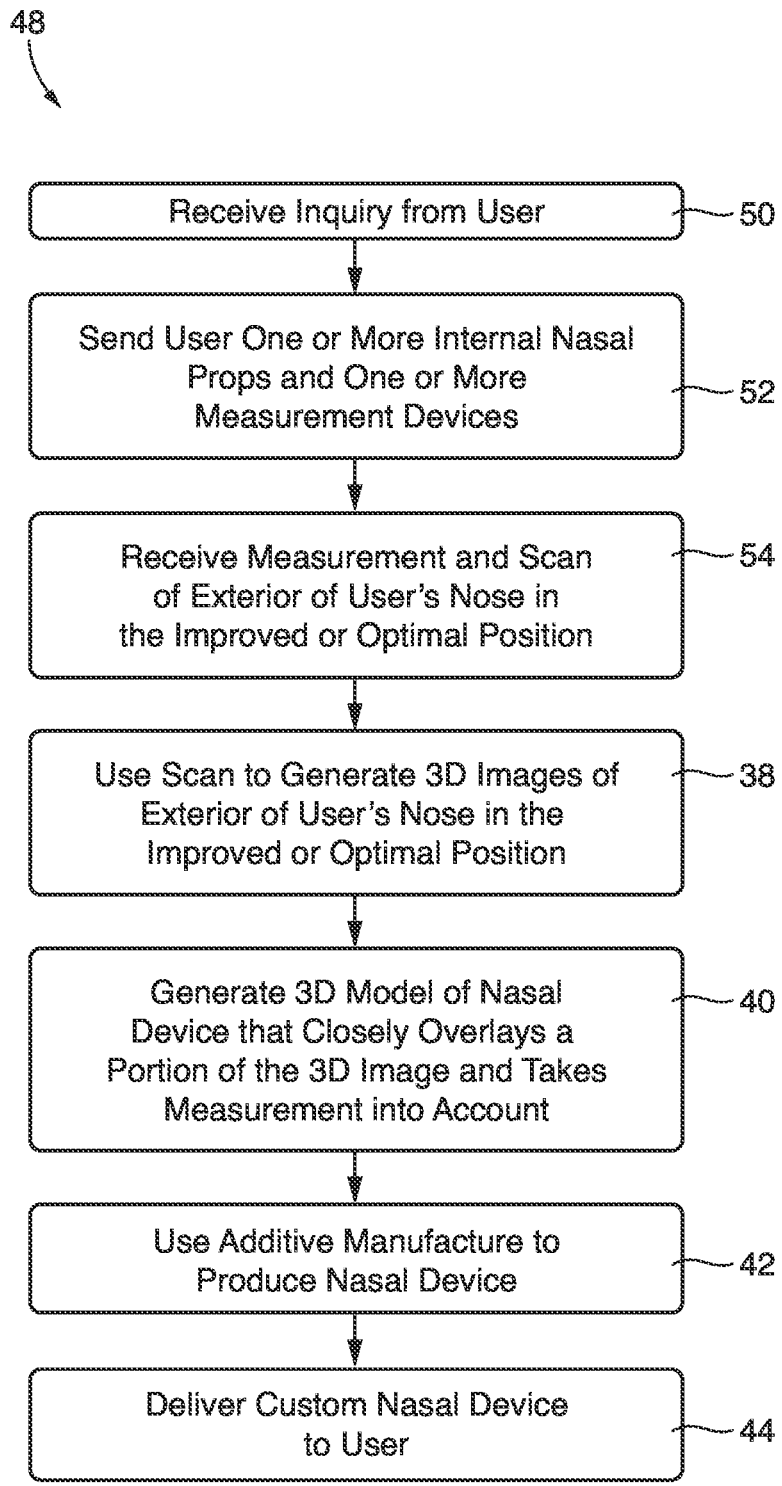
FIG. 9 is a block diagram of an alternative embodiment of a method in accordance with the present invention.

Referring to FIG. 9, in selected embodiments, a method 48 may enable a manufacturer of nasal devices 10 in accordance with the present invention to serve remote users (e.g., users that cannot easily travel to the manufacturer for measurement). Such a method 48 may include receiving 50 an inquiry from a user (e.g., from the user directly or from a healthcare professional associated with the user). In response to the inquiry, a manufacturer may send 52 the user (or a healthcare professional associated with the user) one or more internal nasal props and/or one or more measurement devices. Thereafter, the manufacturer may receive 54 from the user (or a healthcare professional associated with the user) one or more measurements of the thickness of the flexible tissues 20 of the user's nose 16 and/or a digital scan of the exterior of the user's nose 16 in an improved or optimal position for breathing. Accordingly, using the measurement and/or scan, a manufacturer may take steps 38, 40, 42 to deliver 44 (e.g., ship) a custom nasal device 10 to the user.

Figure 10:
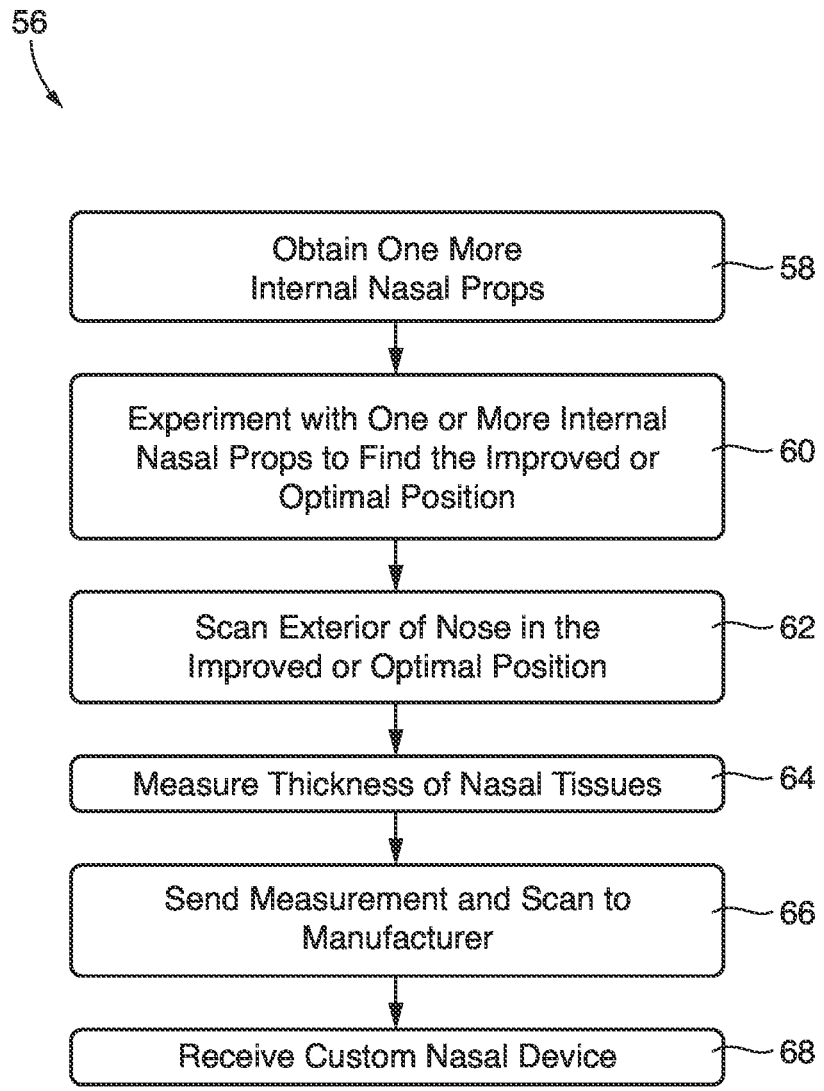
FIG. 10 is a block diagram of another alternative embodiment of a method in accordance with the present invention.
Figure 11:
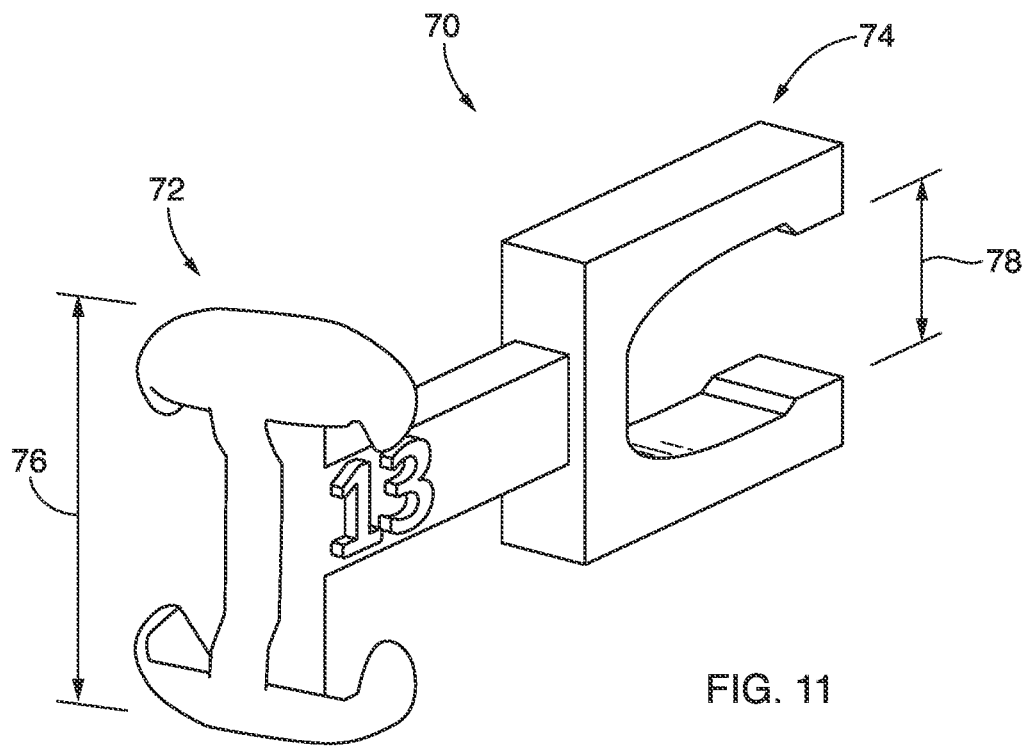
FIG. 11 is a perspective view of one embodiment of a tool in accordance with the present invention with one end of the tool forming an internal nasal prop and the opposite end of the tool forming a measurement device (e.g., a thickness gauge)
Figure 12:
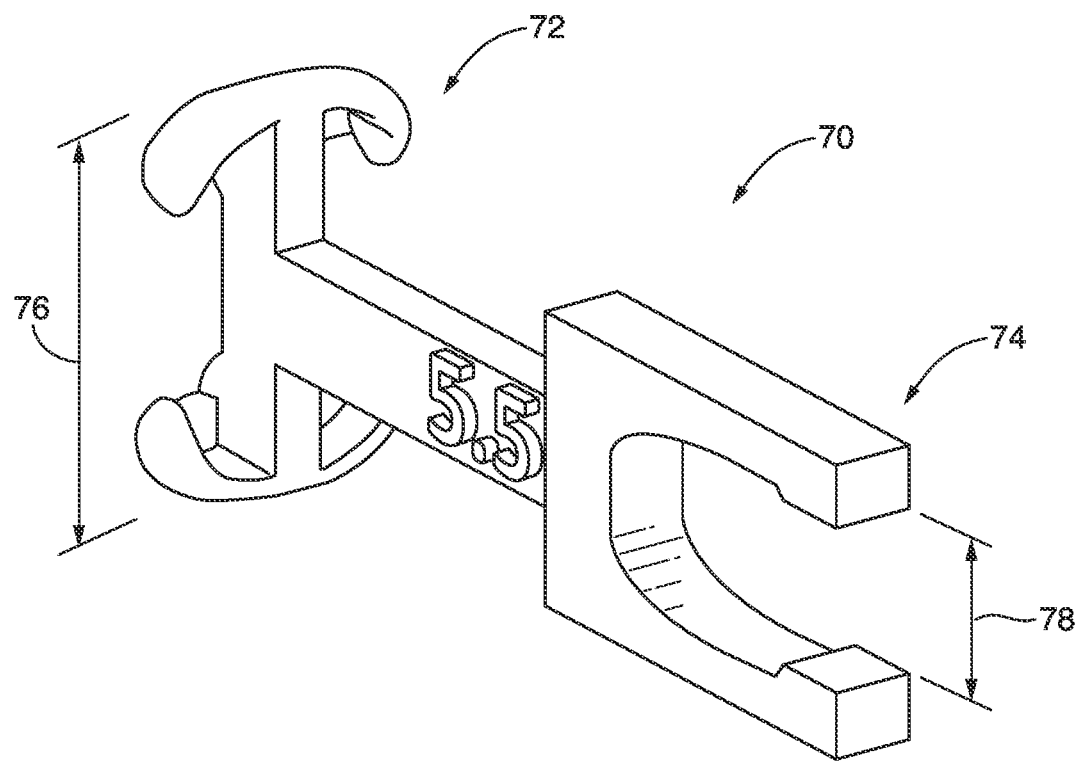
FIG. 12 is another perspective view of the tool of FIG. 11.
Figure 13:
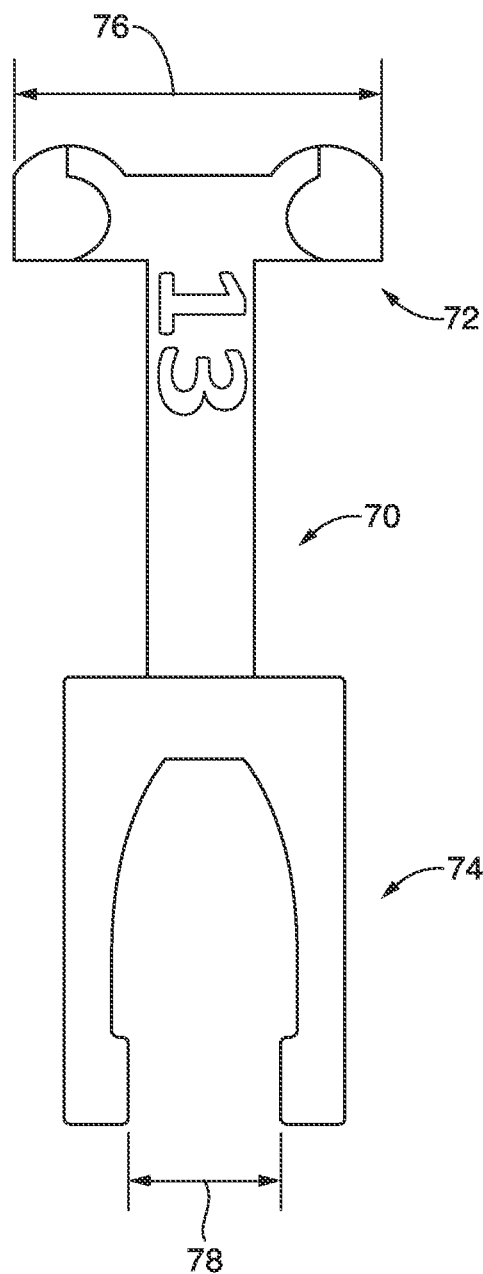
FIG. 13 is a first side view of the tool of FIG. 11.
Figure 14:
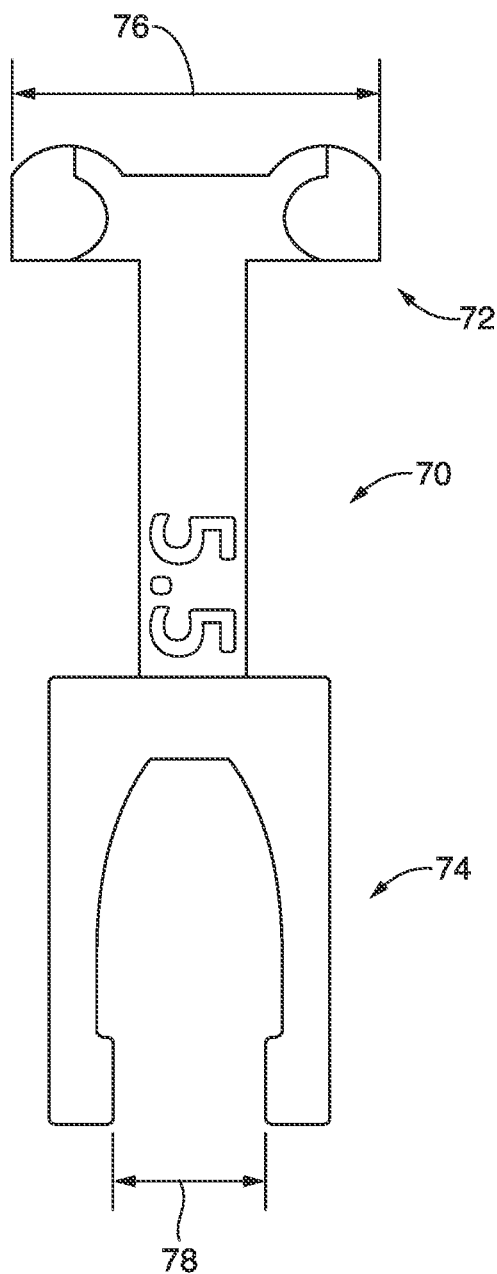
FIG. 14 is a second, opposite side view of the tool of FIG. 11.
Figure 15:
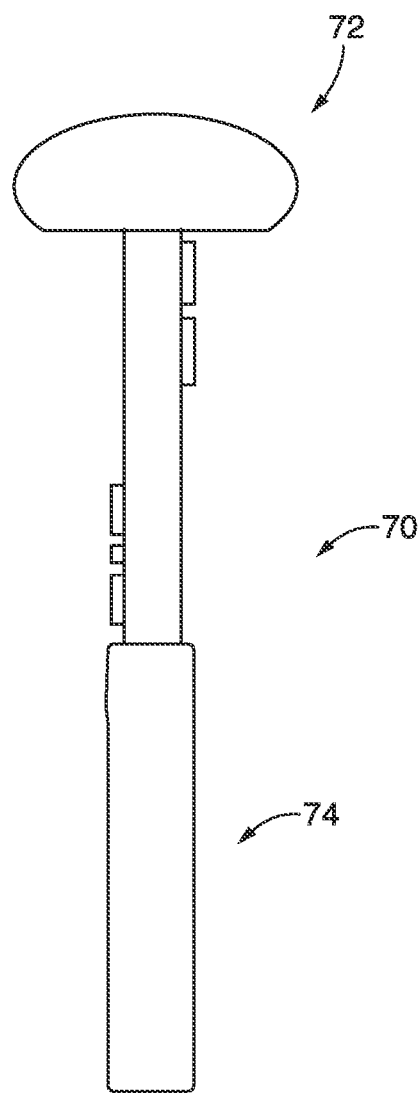
FIG. 15 is a bottom view of the tool of FIG. 11.
Figure 16:
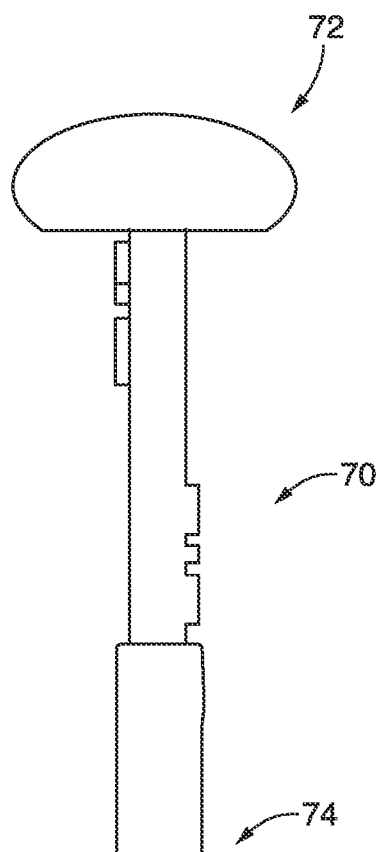
FIG. 16 is a top view of the tool of FIG. 11.
Figure 17:
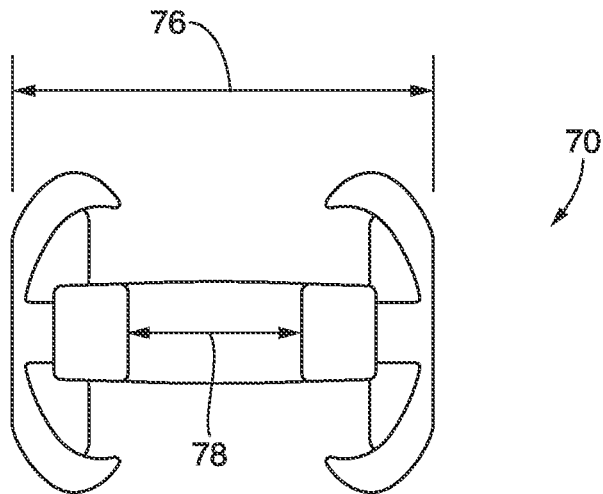
FIG. 17 is a first end view of the tool of FIG. 11.
Figure 18:
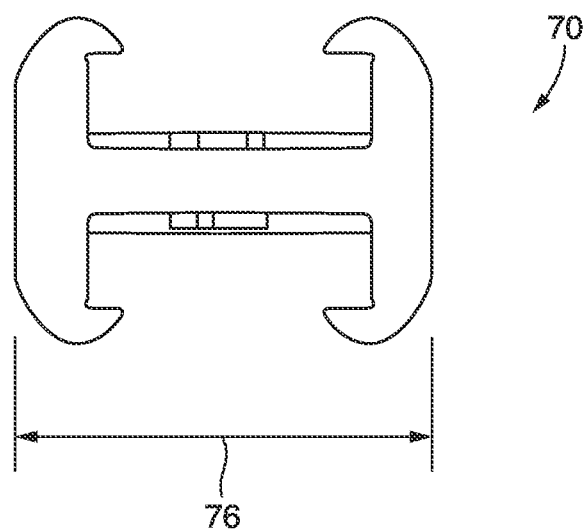
FIG. 18 is a second, opposite end view of the tool of FIG. 11.
Figure 19:
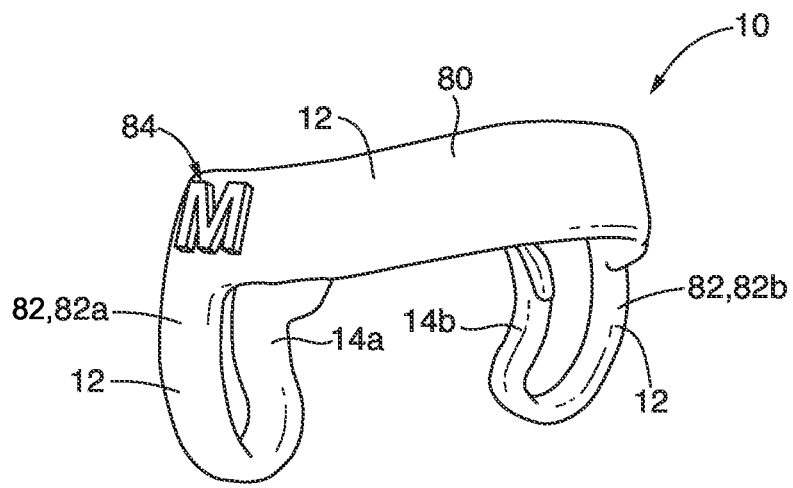
FIG. 19 is a perspective view of an alternative embodiment of a nasal device in accordance with the present invention.
Figure 20:
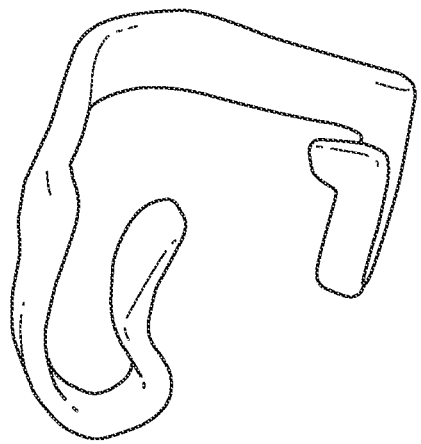
FIG. 20 is another perspective view of the nasal device of FIG. 19.
Figure 21:
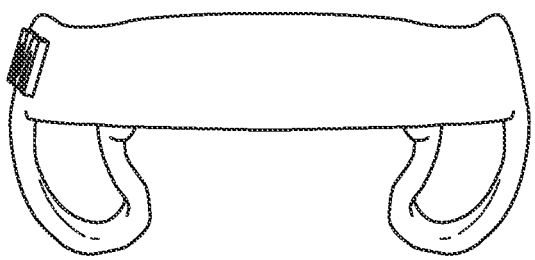
FIG. 21 is a front view of the nasal device of FIG. 19.
Figure 22:
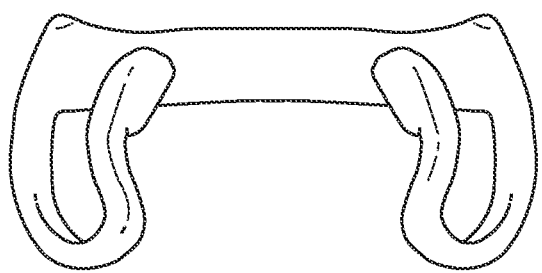
FIG. 22 is a back view of the nasal device of FIG. 19.
Figure 23:
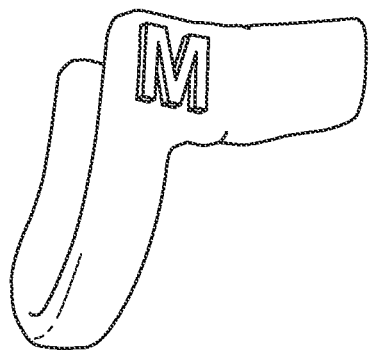
FIG. 23 is a right side view of the nasal device of FIG. 19.
Figure 24:
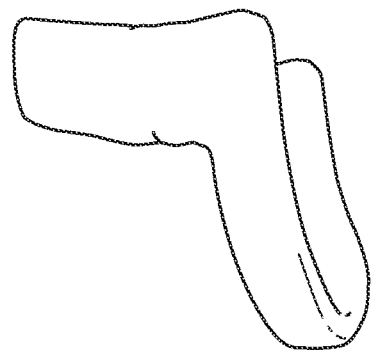
FIG. 24 is a left side view of the nasal device of FIG. 19.
Figure 25:
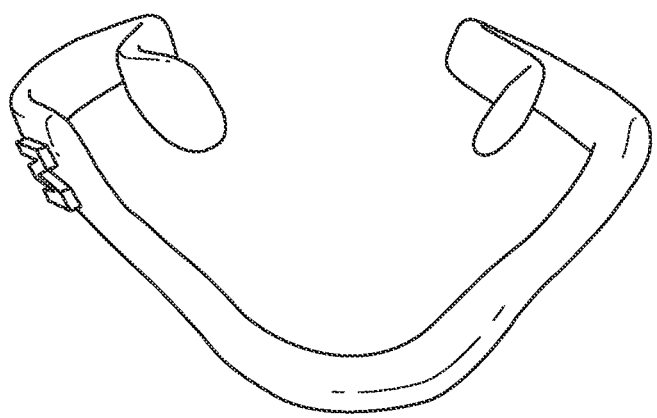
FIG. 25 is a top view of the nasal device of FIG. 19.
Figure 26:
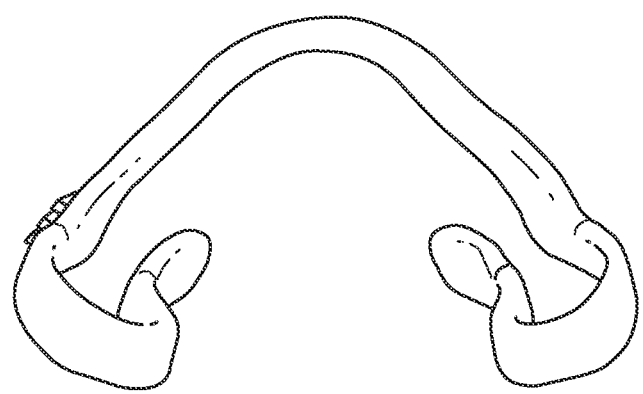
FIG. 26 is a bottom view of the nasal device of FIG. 19.
Figure 27:
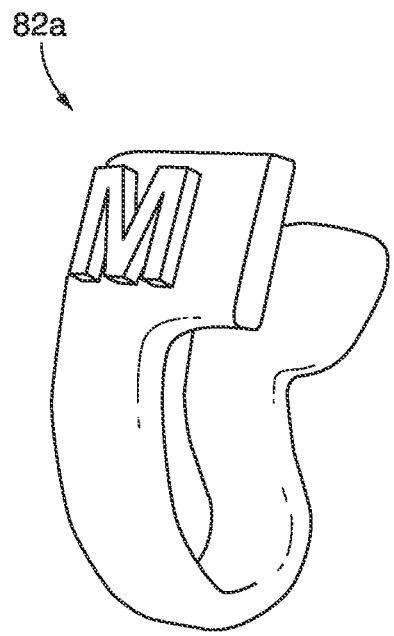
FIG. 27 is a perspective view of a right stock portion of the nasal device of FIG. 19.
Figure 28:
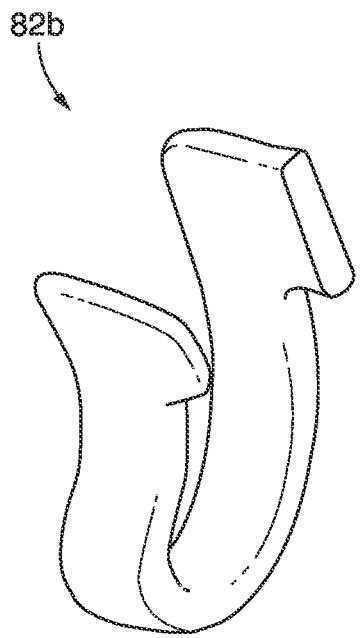
FIG. 28 is a perspective view of a left stock portion of the nasal device of FIG. 19.
Figure 29:
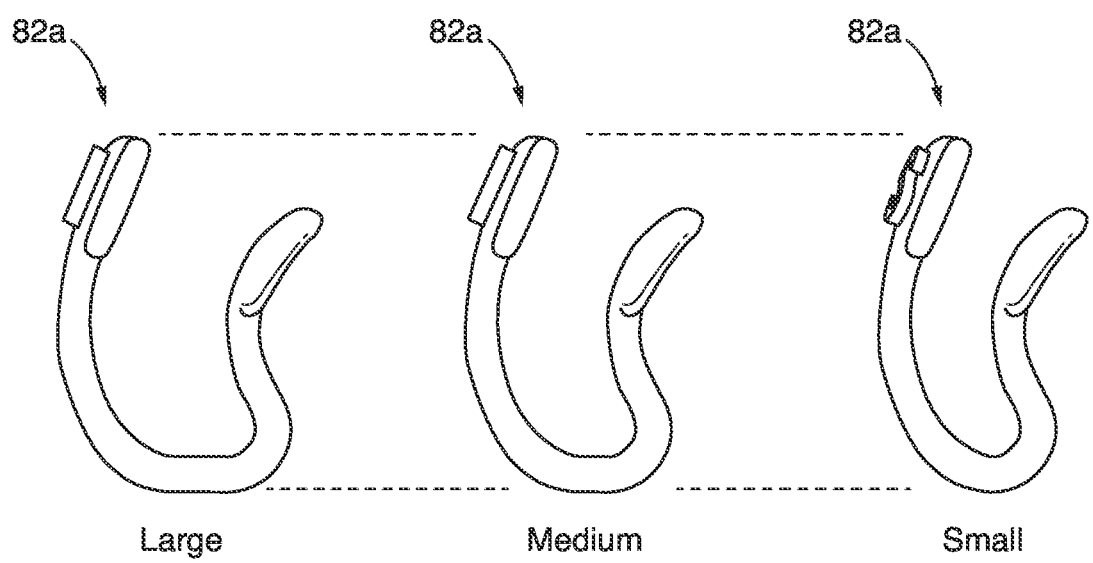
FIG. 29 is a right stock portion in large, medium, and small sizes in accordance with the present invention.

Referring to FIG. 10, in certain embodiments, a method 56 may enable a user to receive a nasal device 10 in accordance with the present invention from a remote manufacturer (e.g., a manufacturer to which the user cannot easily travel for measurement). Such a method 56 may include obtaining 58 one or more internal nasal props. Accordingly, a user may experiment 60 with one or more internal nasal props to find an improved or optimal position for breathing.

For example, in selected embodiments, a user may insert a first internal nasal prop into a first nostril opening and position it therewithin to push and hold (e.g., prop) the flexible tissues 20 outward. A similar process may be followed for a second nostril. The one or more internal nasal props may have various sizes and/or shapes (e.g., pairs of different sizes and/or shapes). Accordingly, a user may experiment 60 with different internal nasal props and/or positioning of those props until the user has identified an improved or optimal position of the flexible tissues 20 corresponding to both nostrils. The improved or optimal position may be a comfortable position wherein the flexible tissues 20 are deflected outward sufficiently to provide an improved or optimal nasal breathing experience for the corresponding user.

Once a user has identified an improved or optimal position of the flexible tissues 20 corresponding to both nostrils, the user may leave the props producing that position in place and then scan 62 the exterior of his or her nose 16. In selected embodiments, a user may use a computerized mobile device (e.g., a smart phone, tablet, or the like) having a camera and running corresponding software to effect the scan. In certain embodiments, such a scan may include the user moving a mobile device during the scan. For example, it may include sweeping a mobile device through a horizontal arc of about 180 degrees from one side of his or her face to the other.

In selected embodiments, a user may measure 64 a thickness (e.g., a distance between an inner surface 26 and an outer surface 28) of the flexible tissues 20 of his or her nose 16. In certain embodiments, a user may use a measurement device to assist in this measuring 64. For example, on or in connection with one or more internal nasal props, a user may obtain one or more gauges of different sizes. By applying different gauges to the flexible tissues 20 of his or her nose 16, a user may determine which gauge fits best. The size indicated on the gauge that fits best may be the thickness of the flexible tissues 20.

Once the scan and the measurement are complete, a user may send 66 the measurement and the scan to a manufacturer. Thereafter, a user may receive 68 a custom nasal device 10 from the manufacturer.

In selected embodiments, an app (e.g., a software application running on a mobile device of a user) may facilitate a method 56 in accordance with the present invention. For example, a user may download an app provided by a manufacturer. Via the app, the user may establish an account and request one or more internal nasal props and/or one or more measurement devices. The app may provide information (e.g., text, videos, etc.) that show a user how to use one or more internal nasal props and/or one or more measurement devices. The app may enable the corresponding mobile device to perform 62 a scan of the exterior of the user's nose 16 once it is in an improved or optimal position. The app may also provide a communication link for sending 66 the scan (e.g., one or more computer files or images), a measurement of the thickness of the flexible tissues 20, payment information, or the like or a combination or sub-combination thereof to the manufacturer.

Referring to FIGS. 11-18, a user may receive one or more internal nasal props and/or one or more measurement devices in the form of one or more tools 70 in accordance with the present invention. In selected embodiments, a tool 70 may have an end that forms of is an internal nasal prop 72. Alternatively, or in addition thereto, a tool 70 may have an end that forms or is a measurement device 74 (e.g., a gauge for determining thickness).

In certain embodiments, multiple tools 70 having internal nasal props 72 and/or measurement devices 74 of different sizes may be provided to a user. For example, in the illustrated embodiment, the internal nasal prop 72 has a height 76 of about 13 mm. The height 72 may be indicated on the tool 70 proximate the internal nasal prop 72. Other internal nasal props 72 may have a height 76 that is larger or smaller than 13 mm. The respective heights of those other internal nasal props 72 may be similarly indicated so that a user can distinguish them from each other. Accordingly, a user may experiment 60 to find an improved or optimal position.

In selected embodiments, an internal nasal prop 72 may have rounded exterior surfaces so that it may be comfortably inserted within a nostril of a user. Additionally, an internal nasal prop 72 may have a relatively slim profile so as to not overly restrict airflow through a nostril when inserted therewithin. Accordingly, a user may breathe through his or her nose 16 with an internal nasal prop 72 inserted within each nostril and, thereby, personally experience how the spacing enforced by the internal nasal props affects (e.g., improves) his or her nasal breathing.

In the illustrated embodiment, the measurement device 74 is a thickness gauge having a gap 78 of about 5.5 mm. The specific size of a gap 78 may be indicated on the tool 70 proximate the measurement device 74. Other measurement devices 74 may have a gap 78 that is larger or smaller than 5.5 mm. The respective gaps 78 of those other measurement devices 74 may be similarly indicated so that a user can distinguish them from each other. Accordingly, a user may slide different measurement devices 74 onto the flexible tissues 20 of his or her nose 16 to find one that fits snugly and/or comfortably. When the best fitting measurement device 74 is identified, the user may identify the thickness measurement by reading it on the corresponding tool 70.

In selected embodiments, an array of tools 70 having internal nasal props 72 and/or measurement devices 74 of various sizes (e.g., various heights 76 and/or gaps 78) in accordance with the present invention may be provided 52 to a user or obtained 58 by a user. Accordingly, a user may have what is needed to find an improved or optimal position and/or measure a thickness of the flexible tissues 20 of his or her nose 16.

Referring to FIGS. 19-29, in selected embodiments, a nasal device 10 in accordance with the present invention may have a customized portion 80 and one or more stock portions 82. In selected embodiments, a stock portion 82 may comprise part of a standard 12 and part of a regulator 14. A customized portion, on the other hand, may only be part of a standard 12. A customized portion 80 may be customized for a particular user. A stock portion 82 may be standardized and used for various users. In certain embodiments, one stock portion 82 may be connected to each end of a customized portion 80. Accordingly, a customized portion 80 may comprise a bridge extending to connect one stock portion 82a to another stock portion 82b.

Stock portions 82 may also be available in right handed versions 82a and left handed versions 82b. Accordingly, when a virtual model of a nasal device 10 is created, a right stock portion 82a may be imported and connected to a right end of a customized portion 80 and a left stock portion 82b may be imported and connected to a left end of the customized portion 80.

Stock portions 82 may be available in different sizes. For example, stock portions 82 may be available in large, medium, and small sizes. The different sizes may correspond to different spacings or gaps between standards 12 and regulators 14. A large size may correspond to a wider gap between a standard 12 and a regulator 14, a smaller size may correspond to a narrower gap between a standard 12 and a regulator 14, etc. Accordingly, when a virtual model of a nasal device 10 is created, a right stock portion 82a of a particular size may be imported and connected to a right end of a customized portion 80 and a left stock portion 82b of the particular size may be imported and connected to a left end of the customized portion 80.

In selected embodiments, one or both stock portions 82a, 82b may include a marking 84 (e.g., an "L" for large, an "M" for medium, and an "S" for small) designating a size thereof. Accordingly, when a nasal device 10 is produced (e.g., printed in an additive manufacturing process) the size thereof may be readily apparent.

Figure 30:
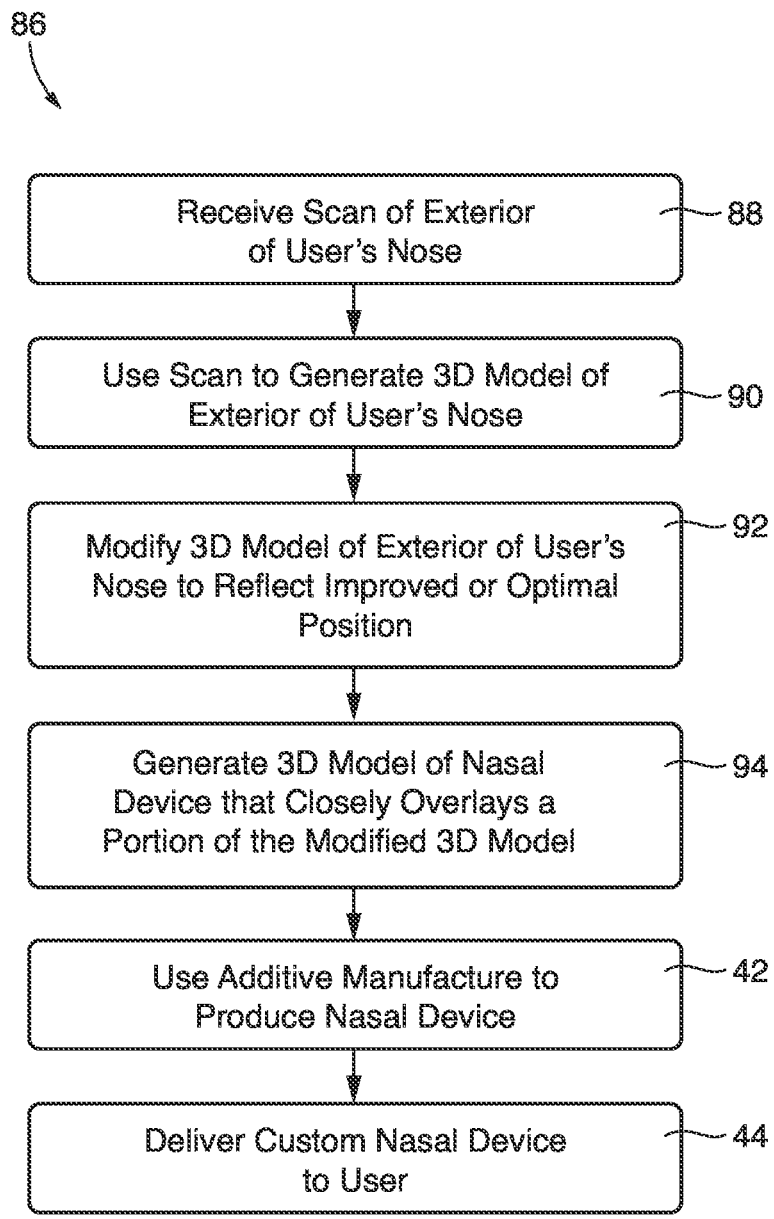
FIG. 30 is a block diagram of another alternative embodiment of a method in accordance with the present invention.

Referring to FIG. 30, in selected embodiments, a method 86 of manufacturing a nasal device 10 may begin with receipt 88 of a digital scan of an exterior of a user's nose. In certain embodiments, a user may use a computerized mobile device (e.g., a smart phone, tablet, or the like) having a camera and running corresponding software to effect the scan. Such a scan may include the user moving a mobile device during the scan. For example, it may include sweeping a mobile device through a horizontal arc of about 180 degrees from one side of his or her face to the other. Thereafter, the user may send the digital scan to a manufacturing entity.

A digital scan may be used to generate 90 a virtual three-dimensional model of a user's nose. Thereafter, this virtual three-dimensional model of a user's nose may be modified 92 or deformed 92 to reflect or portray an improved or optimum breathing position. For example, a technician may use computer software to move (e.g., lift) selected surfaces of the virtual three-dimensional model outward. The selected surfaces may correspond to the flexible tissues 20 on one or both sides of the nose. Accordingly, the original virtual three-dimensional model of a user's nose may correspond to the natural, neutral, or relaxed position of that nose, while the modified virtual three-dimensional model of the user's nose may correspond to an improved or optimum position of the flexible tissues 20 for improved or optimized nasal breathing.

The modified virtual three-dimensional model of the nose may be used to create 94 a virtual three-dimensional model of a nasal device 10. Specifically, a customized portion 80 may be shaped to match the improved or optimized position of the nose 16 of a user. Accordingly, a customized portion 80 may track (e.g., closely follows selected contours of) the nose 16 so positioned. Moreover, one or more stock portions 82 may be digitally defined so as to appropriately fit and extend into corresponding nasal openings 18. For example, a computer-aided drafting (CAD) application or the like may be used to import one or more stock portions 82 into the three dimensional model. The stock portions 82 may be a predefined, standard part. Accordingly, they may be imported and located as desired.

Once a customized portion 80 and one or more stock portions 82 are properly positioned within a virtual three dimensional model, the interfaces between the various components 80, 82 may be filled and/or smoothed so as to provide the desired comfort and functionality. The completed virtual three dimensional model of the nasal device 10 may then be printed 42 in a polymeric material using a three-dimensional printing process. The resulting nasal device 10 may then be delivered 44 to the corresponding user.

In certain embodiments, creating 94 a virtual three-dimensional model of a nasal device 10 may include creating 94 multiple models. For example, in a first model, a customized portion 80 may be connected to two stock portions 82a, 82b that have a large gap. In a second model, a customized portion 80 may be connected to two stock portions 82a, 82b that have a medium gap. Finally, in a third model, a customized portion 80 may be connected to two stock portions 82a, 82b that have a small gap. In such embodiments, three nasal devices 10 (e.g., one with a large gap between a standard 12 and a regulator 14, one with a medium gap between a standard 12 and a regulator 14, and one with a small gap between a standard 12 and a regulator 14) may be additively manufactured 42 and delivered 44 to a user. The user may then try on the various nasal devices 10 and use the one that is most beneficial, comfortable, or the like. The others devices 10 may be discarded. Should the user need a replacement, he or she may just order the size that suited him or her best.

In selected embodiments, an app (e.g., a software application running on a mobile device of a user) may facilitate a method 86 in accordance with the present invention. For example, a user may download an app provided by a manufacturer. Via the app, the user may establish an account. The app may provide information (e.g., text, videos, etc.) that show a user how to perform a digital scan of the exterior of the user's nose 16. The app may also provide a communication link for sending 66 the scan (e.g., one or more computer files or images), payment information, or the like or a combination or sub-combination thereof to the manufacturer.

Figure 31:
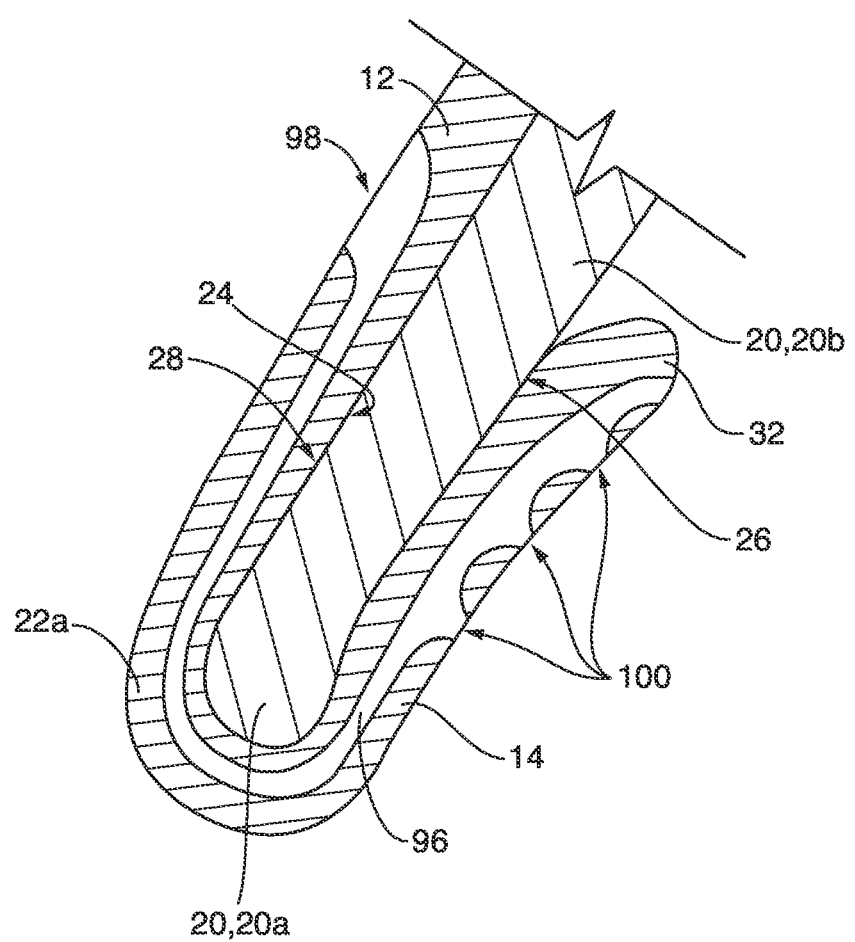
FIG. 31 is a cross-sectional view of a portion of another alternative embodiment of a nasal device in accordance with the present invention.

Referring to FIG. 31, in selected embodiments, a nasal device 10 or some portion thereof (e.g., one or more stock portions 82) may include a conduit 96 extending from an exterior aperture 98 (e.g., an aperture 98 located on exterior to the nose 16 of the user) to one or more interior apertures 100 (e.g., one or more apertures 100 located on interior to or proximate an interior of the nose 16 of the user). Liquids (e.g., medications, aroma therapy products, "essential" oils, or the like) applied to an exterior aperture 98 may travel (e.g., wick or move through capillary action) through the conduit 96 and exit (e.g., vaporize) through one or more exit apertures 100. In selected embodiments, wicking or sponge material may be included at the exterior aperture 96, the one or more interior apertures 100, and/or within the conduit 96 to facilitate the absorption, movement, and/or evaporation of the liquids. Accordingly, a nasal device 10 may be a mechanism for delivering medication, fragrances, or the like to a user.

Figure 32:
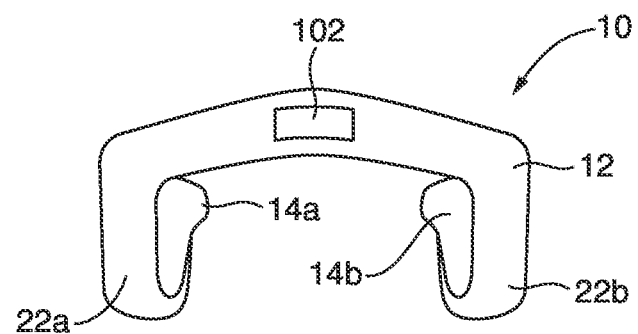
FIG. 32 is a front view of another alternative embodiment of a nasal device in accordance with the present invention.

Referring to FIG. 32, in selected embodiments, a nasal device 10 may include a radio frequency temperature sensor 102. In response to being activated by electromagnetic waves, such a sensor 102 may report (e.g., wirelessly transmit) a temperate of the user.

Figure 33:
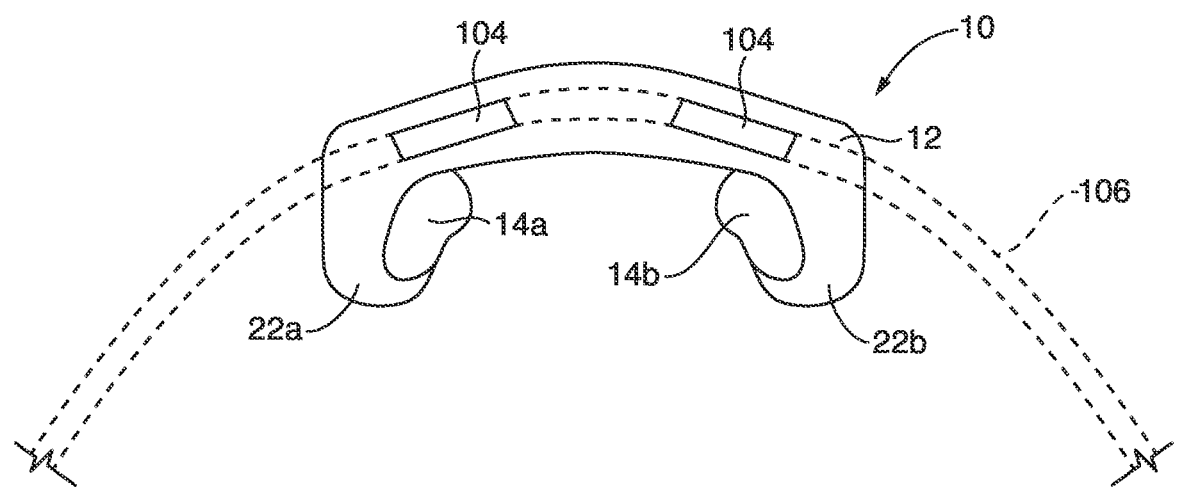
FIG. 33 is a front view of another alternative embodiment of a nasal device in accordance with the present invention.

Referring to FIG. 33, in certain embodiments, a nasal device 10 may include one or more engagement mechanisms 104 for receiving and/or securing a rim 106 of a face mask therewithin. In selected embodiments, such a rim 106 may be additively manufactured from a virtual three-dimensional model built to closely and comfortable follow the face of a user. That is, the rim 106 may be built based on a digital scan of the face of the user. Accordingly, a nasal device 10 may assist in securing a mask to a user (e.g., aid one or more elastic or ties in securing the mask to the user) and prevent the mask from deforming the nose of the user in a manner that restricts nasal breathing.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method comprising:
   receiving a digital scan of an exterior of a nose of a user, wherein the exterior of the nose includes one or more exterior surfaces corresponding to flexible tissues on one or both sides of the nose;
   producing, based on the digital scan, a virtual three-dimensional model of the exterior of the nose, the virtual three-dimensional model positioning the one or more exterior surfaces in an improved position, the one or more exterior surfaces in the improved position being deflected outward with respect to the one or more exterior surfaces in a relaxed, neutral position of the nose;
   producing, based on the virtual three-dimensional model of the exterior of the nose, a virtual three-dimensional model of a nasal device customized to fit the nose in the improved position; and
   using an additive manufacturing process to produce the nasal device.

2. The method of claim 1, further comprising delivering the nasal device to the user.

3. The method of claim 2, wherein the delivering comprises shipping the nasal device to the user.

4. The method of claim 1, wherein the improved position provides for improved nasal breathing with respect to the relaxed, neutral position.

5. The method of claim 1, wherein the nose in the digital scan comprises the one or more exterior surfaces in the improved position.

6. The method of claim 1, wherein the nose in the digital scan comprises the one or more exterior surfaces in a relaxed in the relaxed, neutral position.

7. A method comprising:
   receiving a digital scan of an exterior of a nose of a user, wherein the exterior of the nose includes one or more exterior surfaces corresponding to flexible tissues on one or both sides of the nose;
   producing, based on the digital scan, a first virtual three-dimensional model of the exterior of the nose;
   deforming the first virtual three-dimensional model to produce a second virtual three-dimensional model of the exterior of the nose, the deforming comprising moving one or more modeled surfaces of the second virtual three-dimensional model outward;
   producing, based on the second virtual three-dimensional model, a virtual three-dimensional model of a nasal device; and
   using an additive manufacturing process to produce the nasal device with a rigidity sufficient to flex the flexible tissues rather than be flexed by the flexible tissues.

8. The method of claim 7, further comprising delivering the nasal device to the user.

9. The method of claim 7, wherein;
   the one or more modeled surfaces correspond to the one or more exterior surfaces.

10. The method of claim 7, wherein the virtual three-dimensional model of the nasal device comprises a customized portion, a first stock portion connected to a first end of the customized portion, and a second stock portion connected to a second end of the customized portion.

11. The method of claim 10, wherein the customized portion extends from a first side of the nose of the second virtual three-dimensional model to a second side of the nose of the second virtual three-dimensional model.

12. The method of claim 11, wherein the customized portion is customized to fit the second virtual three-dimensional model of the exterior of the nose.

13. The method of claim 12, wherein the first stock portion and the second stock portion are standardized components.

14. The method of claim 13, wherein the producing comprises importing the first stock portion and the second stock portion and positioning the first stock portion and the second stock portion with respect to the second virtual three-dimensional model of the exterior of the nose.

15. A method comprising:
   receiving a digital scan of an exterior of a nose of a user;
   producing, based on the digital scan, a first virtual three-dimensional model of the exterior of the nose;
   deforming the first virtual three-dimensional model to produce a second virtual three-dimensional model of the exterior of the nose, the deforming comprising deflecting outward one or more surfaces corresponding to flexible tissues on one or both sides of the nose;
   producing a virtual three-dimensional model of a nasal device by
      positioning a right stock portion with respect to a right nostril of the nose in the second virtual three-dimensional model,
      positioning a left stock portion with respect to a left nostril of the nose in the second virtual three-dimensional model, and
      creating a customized portion that follows a contour of the nose in the second virtual three-dimensional model and extends to connect the right stock portion to the left stock portion; and using an additive manufacturing process to produce the nasal device.

* * * * *